United States Patent [19]

Ladanyi

[11] 4,406,881

[45] Sep. 27, 1983

[54] ANTIMICROBIAL AGENT

[75] Inventor: Peter A. Ladanyi, Fort Collins, Colo.

[73] Assignee: Vipont Laboratories, Fort Collins, Colo.

[21] Appl. No.: 303,389

[22] Filed: Sep. 18, 1981

Related U.S. Application Data

[63] Continuation of Ser. No. 151,706, May 20, 1980, abandoned, which is a continuation of Ser. No. 24,604, Mar. 28, 1979, abandoned.

[51] Int. Cl.³ .................. A61K 7/16; A61K 33/30
[52] U.S. Cl. ................................. 424/49; 424/145
[58] Field of Search ............................. 424/49, 145

[56] References Cited

U.S. PATENT DOCUMENTS

| 2,344,830 | 3/1944 | Motts | 424/195 |
|---|---|---|---|
| 209,331 | 10/1878 | Daniel | 424/195 |
| 4,145,412 | 3/1979 | Ladawyi | 424/58 |

PUBLICATIONS

Chemical Abstracts 46: 11332f (1952).
Chemical Abstracts 52: 7432h (1958).

*Primary Examiner*—Jerome D. Goldberg
*Attorney, Agent, or Firm*—Eric P. Schellin

[57] ABSTRACT

An antimicrobial agent comprising a mineral acid salt of a benzophenanthridine alkaloid in a mixture with zinc chloride.

12 Claims, No Drawings

4,406,881

ANTIMICROBIAL AGENT

This is a continuation of application Ser. No. 151,706 and now abandoned filed May 20, 1980, which is a continuation-in-part of Ser. No. 024,604, and now abandoned filed Mar. 28, 1979.

BACKGROUND OF THE INVENTION

This invention relates to the composition and preparation of an antimicrobial agent which may be used in dental preparations, surgical and other soaps, various other topical preparations, injectable medicines, and other drug applications. In particular the invention relates to compositions containing mineral acid salts of benzophenanthridine alkaloids mixed with a metal salt.

One of the important sources of sanguinarine is a perennial herb native to North America called *Sanguinaria canadensis* Linne (Family: Papvaraceae) commonly known as blood root, red root, puccoon etc. The plant contains benzophenanthridine alkaloids including sanguinarine, chelerythrine, and several others. The major alkaloids present are sanguinarine and chelerythrine. The eighth edition of the Merck Index lists the alkaloids as sanguinarine, chelerythrine, protopine and homochelidonine. The pure chemicals sanguinarine, chelerythrine, and other benzophenanthridine alkaloids can be isolated from other plants besides Sanguinaria. Also, they are available, even though very rarely, from some chemical supply houses. Semi-purified forms of the alkaloids are commercially available, and these are generally referred to as sanguinarine nitrate and sanguinarine sulfate. These "salts" are the salts of the mixed alkaloids of the plant Sanguinaria: mainly sanguinarine, chelerythrine, and protopine. While few references can be found in the literature regarding the usage of any of the pure benzophenanthridine alkaloids, plants containing such compounds have been used for medical purposes for quite some time for a wide variety of ailments.

The principle use of sanguinarine up to recently was a stimulant expectorant to cough syrups containing "sanguinarine nitrate".

The use of sanguinarine with thiophosphoric acid in various animal and human neoplasms is shown in French patents, number 70-22029 and 2,152,972.

The alkaloid sanguinarine in solution has been shown to have some antifungal and antiprotozoan properties. The sanguinarine is applied as an emulsion topically to fungal infections. The antibacterial activity of sanguinarine has been found to vary with the attached radicals, and various salts of sanguinarine have been shown to have some activity. The hydrochloride and the sulfate salts have been found to have some activity against certain bacteria at various concentrations. Sanguinarine nitrate is reported to have some weak bacteriostatic action on various types of bacteria.

SUMMARY OF THE INVENTION

The present invention relates to the preparation and the use of antimicrobial agents, formed particularly from mineral acid salts of benzophenanthridine alkaloids and a zinc salt and useful in dental preparations, mouthwashes, rinses, surgical soaps, shampoos, creams, lotions, powders, injectables, etc., and other forms of drug preparation and disinfectants. The mineral acid salts of the benzophenanthridine alkaloids may be used in various concentrations with zinc chloride or a similar substance as an antimicrobial agent for use in treating both human and animal infections and diseases.

It is therefore, among the objects and advantages of the present invention to provide an antimicrobial agent of mineral acid salts of a benzophenanthridine alkaloid and a zinc salt, useful for topical administration, injectables and other forms of drug preparations.

Another object of the invention is to provide a benzophenanthridine alkaloid salt zinc preparation for treatment of periodontal disease, prevention of dental caries and similar oral cavity impairments.

Still another object of the invention is to provide drug preparation of a benzophenanthridine alkaloid and a salt zinc, useful for treatment of ringworm infections, acne, cold sores and various parasitic infections.

Yet another object of the invention is to provide a drug preparation of a benzophenanthridine alkaloid and a salt zinc, useful for treatment of scours in animals.

These and other objects and advantages of the invention may be readily ascertained by the following description and examples of the preparation of the invention.

PREPARATION OF ANTIMICROBIAL AGENT

The pure chemical, either sanguinarine, chelerythrine, or other benzophenanthridine alkaloids, is dissolved in a chloroform/methanol mixture and acidified with a mineral acid such as hydrochloric acid. The acidic mixture is evaporated to dryness and the residue is recrystallized from ethyl alcohol/chloroform, 50/50.

For use, the mineral acid salt of the benzophenanthridine alkaloid is dissolved in either deionized water or $C_1$–$C_6$ alcohols, glycerine, propylene glycol, petrolatum, or other organic solvents at 70 degrees C., and zinc chloride is added to the above solutions. The preparations generally contain 0.1% by weight and up to 10% by weight of the benzophenanthridine alkaloid salt, and at least 35% and up to 60% by weight zinc chloride, with the remainder being the solvent. The material can be diluted to the desired concentration, depending on the type of use, with the solvents listed above.

The benzophenanthridine alkaloid salt is used in preparations containing 0.1%–10% benzophenanthridine by weight. The zinc chloride is present in amounts ranging from about 2% to about 60%. The lower concentrations are generally effective in the treatment of most diseases as explained below.

An example of a basic preparation:

| | |
|---|---|
| sanguinarine chloride | 0.3% |
| glycerine U.S.P. | 64.7% |
| zinc chloride AR. | 35.0% |

The basic preparation can be varied by using, in place of sanguinarine chloride, 0.3% of another mineral acid salt of a benzophenanthridine alkaloid, such as chelerythrine chloride.

A second example of a preparation is:

| | |
|---|---|
| sanguinarine chloride | 1.0% |
| glycerine U.S.P. | 96.0% |
| zinc chloride AR. | 3.0% |

A third example of such a preparation is:

| | |
|---|---|
| sanguinarine chloride | 1.0% |

| | |
|---|---|
| glycerine U.S.P. | 64.0% |
| zinc chloride AR. | 35.0% |

A fourth example of such a preparation for dental use is:

| | |
|---|---|
| sanguinarine chloride | 1.0% |
| glycerine U.S.P. | 95.6% |
| zinc chloride AR. | 3.0% |
| stannous fluoride | 0.4% |

Numerous types of diseases were treated in humans and in animals with the composition of the present invention as follows:

EXAMPLE 1

Canine Ringworm

A 5%–10% solution of the first basic preparation was used, applied directly to the infected area, one to three applications as indicated, 48 hours apart.

EXAMPLE 2

Feline Ringworm

A 4%–8% solution of the first basic preparations was applied directly to the infected area, 48 hours apart up to three applications.

EXAMPLE 3

Bovine Ringworm

The etiological agent of this involvement is usually the mold known as Trychophyton album. The duration of the disease is 4–12 months.

A 30% dilution of the first basic preparation is used, applied directly to the involved areas, 48 hours apart. Three applications proved to be adequate in treating the condition successfully.

EXAMPLE 4

Bovine Neo-natal Diarrhea

Twelve animals having diagnosed and confirmed neo-natal diarrhea were treated with 0.75 grams of the first basic preparation orally, once per animal, and showed clinical cure with one exception.

This constitutes an excellent result, considering that conventional antibiotic therapy currently in use has a much lower percentage of success.

Sanguinarine chloride and chelerythrine chloride have strong antimicrobial properties. Zinc chloride has antimicrobial properties only in high concentrations. It can be seen from Table I that sanguinarine chloride mixed with zinc chloride in a 1:1 ratio, as a rule, did not show a synergistic effect or even as additive action against most microorganisms tested in vitro. Further, it was found that in most cases the antimicrobial action of the sanguinarine chloride and zinc chloride mixture depended mostly on the amount of sanguinarine chloride present in the mixture, and was relatively independent from the amount of zinc chloride.

TABLE I

| | Mean inactivating dose in micrograms per milliliter ($\mu g/ml$) of media. | | |
|---|---|---|---|
| Microorganism | $ZnCl_2$ | Sanguinarine Chloride | $ZnCl_2$ & Sanguinarine Chloride (1:1) |
| Bacillus subtilis | 25,000 | 22 | 1,000 |
| Escherichia coli | 6,250 | 270 | 500 |
| Klebsiella pneumoniae | 3,125 | 540 | 1,000 |
| Proteus vulgaris | 12,500 | 590 | 1,000 |
| Staphylococcus aureus | 6,250 | 70 | 500 |
| Streptococcus faecalis | 25,000 | 393 | 500 |
| Streptococcus mutans | 1,563 | 161 | 63 |
| Candida albicans | — | 150 | — |
| Saccharomyces cerevisiae | 6,250 | 20 | 63 |
| Pseudomonas aeruginosa | 3,500 | 7,000 | 400 |

A separate test was conducted to determine the inhibitory concentration of sanguinarine chloride alone. These concentrations, for microorganisms in vitro, are as follows:

100 micrograms per milliliter for Escherichia coli
100 micrograms per milliliter for Candida albicans
50 micrograms per milliliter for Streptococcus mutans
10 micrograms per milliliter for Staphylococcus aureus It was further found that a concentration of sanguinarine chloride of 25 micrograms per milliliter caused a 100% reduction of dental plaque by inactivating plaque forming microorganisms freshly collected from human dental plaque. Sanquinarine chloride compared favorably in vitro to chlorhexidine (Hibitane ®), a material used as a standard in evaluating inhibition of human dental plaque forming microorganisms.

However, under in vivo test conditions, sanguinarine chloride was found to be ineffective against plaque forming microorganisms.

When sanguinarine chloride was applied to the affected area of both dogs and humans, repeated treatment with sanguinarine chloride alone did not reduce dental plaque or alleviate the symptons of gingivitis or periodontal disease. Continuous treatment with sanguinarine chloride did not prevent the accumulation of dental plaque on teeth or prevent the occurrence of periodontal disease. However, it has been found that a combination of sanguinarine chloride and zinc chloride in glycerine is effective in vivo in reducing dental plaque and the incidence of periodontal disease, and has shown definite promise in the treatment and prevention of human periodontal disease.

Results of tests on guinea pigs with induced ringworm infection, dogs with periodontal disease, and humans with periodontal disease have shown that glycerine preparations of sanguinarine chloride plus zinc chloride are far superior for the management of infections in vivo than either zinc chloride or sanguinarine chloride alone.

The above phenomenon is not what would be expected, in light of the in vitro test results. In most cases sanguinarine chloride in vivo was only slightly effective or not at all. This was quite unexpected considering that in vitro all the antimicrobial activity of a sanguinarine chloride-zinc chloride mixture could be explained by the amount of sanguinarine present in the mixture.

Controlled clinical tests on 24 male beagle dogs showed that after four weeks of treatment the dogs treated with the zinc chloride-sanguinarine chloride-glycerine mixture had the lowest plaque and gingivitis scores, while the dogs treated with sanguinarine chloride alone had the highest. The dogs were treated topically once daily with the respective test formulation.

The results presented in Table II clearly indicate that the sanguinarine chloride-zinc chloride in glycerine treated group of dogs had lower gingivitis scores after four weeks of treatment than did the other groups. Zinc chloride alone was slightly active, but sanguinarine chloride alone showed no activity in vivo at all. This result is unexpected, considering that, in vitro, sanguinarine chloride is quite effective against microorganisms.

TABLE II

Oral Clinical Studies - Beagles (dogs)

| Treatment | 0 (start) | After 4 weeks |
|---|---|---|
| Mean Gingivitis Scores | | |
| None | 0.475 | 0.91 |
| 0.1% Sanguinarine chloride | 0.495 | 0.942 |
| 2.7% Zinc chloride | 0.44 | 0.75 |
| 0.1% Sanguinarine chloride with 2.7% zinc chloride in glycerine | 0.418 | 0.548 |
| Mean Plaque Scores | | |
| None | 7.478 | 12.408 |
| 0.1% Sanguinarine chloride | 8.885 | 12.89 |
| 2.7% Zinc chloride | 8.76 | 10.15 |
| 0.1% Sanguinarine chloride with 2.7% zinc chloride in glycerine | 8.578 | 7.407 |
| Mean Pocket Depths | | |
| None | 1.459 | 1.458 |
| 0.1% Sanguinarine chloride | 1.415 | 1.48 |
| 2.7% Zinc chloride | 1.46 | 1.37 |
| 0.1% Sanguinarine chloride with 2.7% zinc chloride in glycerine | 1.445 | 1.44 |

Similar results occured, when the dogs were evaluated for the return of dental plaques (See Table 2, for plaque scores), sanguinarine chloride alone was not active in vivo. Zinc chloride was slightly preventive but the preparation of sanguinarine chloride-zinc chloride in glycerine not only prevented the return and further proliferation of dental plaque but significantly further reduced it during the four weeks of treatment.

Data also indicate that even the pocket depths were reduced somewhat by the treatment materials containing zinc chloride in glycerine, or zinc chloride-sanguinarine chloride in glycerine.

In a clinical test involving twenty volunteer patients with periodontal disease, it was observed that after treatment with benzophenanthridine alkaloid chloride-zinc chloride in glycerine, there was rapid improvement. Inflammation, infection and pockets were eliminated, abcesses ceased, gingival tone greatly improved, tissues healed, and in some cases normal tissue was restored and teeth mobility was reduced.

The clinical studies above showed that sanguinarine chloride in vivo was only slightly antimicrobial, very slow acting, or had no effect on the course of the infection at all.

Zinc chloride in the concentrations required in vivo to have antimicrobial action caused blanching of tissue and, in some cases, chemical burns and other tissue damage. Further, zinc chloride was found to be slow acting in vivo as an antimicrobial agent.

Glycerine preparations containing sanguinarine chloride or other benzophenathridine alkaloids and zinc chloride were fast acting, requiring only one to three applications to clear out infections rapidly. Further, these preparations did not appear to have the undesirable side effects of the zinc chloride in the concentration necessary to achieve antimicrobial effectiveness.

EXAMPLE 5

Human Periodontal Disease

It has been reported that periodontal (gum) disease affects 2 out of 3 middle-aged Americans. Destruction of the tissue and structures that hold teeth fast in their sockets accounts for 75% of tooth loss after the age of 40. Most cases of periodontal disease are the result of neglect and can be largely prevented by a regular program of thorough hygiene. In the most common type of periodontal disease, the three chief culprits are bacteria, calculus (tartar), and food debris.

This invention has been used by dentists in clincial management of over forty cases of various types of human periodontal disease.

In some cases, even a single treatment brought major improvement in the condition of the diseased gums. Clinical cure resulting from the treatment was quite apparent and included: elimination of inflammation, normal tissue tone restored, pockets were eliminated, infections were cleared up, mobility was reduced, and gingival tone was greatly improved.

The materials and methods used were the following:

1. Undiluted Paste for Packing:

In cases of widespread tissue involvement, undiluted preparation was used in quantity sufficient (q.s.) to "cover" or "pack" the infected or inflamed areas of gingival tissues.

The clinical procedure consisted of two treatments approximately two weeks apart, with the application of not less than 1.0 mm thickness of the basic preparation to the diseased periodontium. In cases where undiluted material was used, it was either applied topically with a spatula or 0.25 ml was pressed through a 22 gauge needle attached to a 1.0 ml pressure syringe. The material was introduced into the gingivae to the attachment (q.s.) to fill the pocket and the medication was left in place for 10-15 minutes.

2. String Technique: Cotton String Saturated with the Drug Preparation:

In cases where individual teeth were to be treated, an ordinary soft cotton string, sterilized before use, or "gingipak" was used (gingipak contains racemic epinephrine hydrochloride 8-100 solution and 1% benzyl alcohol as preservative).

Cotton strings 1-1.5 cm in length were saturated with undiluted material by using a spatula and precut pieces of string which were then impregnated on a dentist's mixing pad. These strings, when properly impregnated with the preparation, weigh approximately 35 mg/cm.

One to three strings were used per tooth depending upon the circumference of the tooth. Up to three strings were sometimes used for a total of approximately 105 mg of the preparation. Impregnated strings were left in place 10-15 minutes.

Dental floss or similar substrate, such as synthetic hollow fiber string, can be impregnated with the basic preparation for use in treating the teeth and gums.

3. Dilution of Paste for Irrigation:

In addition to "packing" of the periodontium or employing the "string technique" on individual teeth, irrigation was often used concurrently as part of regimen. Generally, the diseased periodontium was first packed with undiluted preparation or the teeth were individually treated by the string technique described above.

These methods of treatment were followed by irrigation with a suspension of the preparation in either water or glycerine. Suspensions were prepared to contain 1 part of full strength material to 1 part of glycerine, or 1 part of water depending on whether a glycerine or water suspension was desired. The final suspension was V/V mixture of 1 part material to 1 part diluent. Irrigation was accomplished by filling a 7.0 ml syringe to contain 420 mg of the suspension. For treatment of individual teeth, a total of 1.0 ml of material in suspension was used to irrigate the buccal, lingual, and interproximal areas about the tooth. Where indicated, all teeth were irrigated with 840 mg of the suspension contained in two syringes.

EXAMPLE 6

Dental Carier

Preparations containing about 0.3% sanguinarine chloride and about 35% zinc chloride were used on seven patients with dental caries.

Decay was removed from the teeth with a spoon excavator leaving a layer of carious tissue about 1 mm to 1½ mm in depth. The antimicrobial preparation was placed over the remaining decay, about 57.1 mg of preparation, with a Hollenbeck carver and uniformly applied over the decayed area with a piece of cotton held in cotton tweezers. Intermediate restorative material (IRM) was used as a temporary restoration to seal the material in the cavity preparation.

After several weeks (6 weeks) specimens for bacteriological and histological studies, including electron microscopy, were undertaken.

The conclusions of the investigators were that the preparation could be considered a cariostatic agent. Further, the material may enhance sclerotic dentine formation, thus forming a hard protective floor between the carious lesion and the pulp.

The benzophenanthrine chloride-zinc chloride-glycerine composition can be used in conjunction with a fluoride-providing compound. These compounds are characterized by the ability to release fluoride ions in water and by substantial freedom from reaction with other compounds present in the oral preparation. Among these materials are inorganic fluoride salts such as suitable alkali metal, alkaline earth metal, and heavy metal salts. Alkali metal and tin fluorides, such as sodium and stannous fluorides, and mixtures thereof, are preferred.

The amount of the fluoride-providing compound is dependent to some extent upon the type of compounds, its solubility, and the type of oral preparation, but it must be nontoxic amount. Any suitable minimum amount of such compound may be used, but it is preferable to employ sufficient compound to release from 0.005% to 1%, most preferably about 0.1% by weight of fluoride ion. Typically, in the cases of alkali metal fluoride and stannous fluoride, this component is present in an amount up to 3% by weight, based on the weight of the preparation, and preferaby in the range of from 0.05% to 1%.

EXAMPLE 7

Antimicrobial Activity

In order to illustrate the antimicrobial effectiveness of the composition according to the present invention, a series of in vitro and in vivo tests were performed. These tests were designed to demonstrate the lowest concentration of sanguinarine chloride that will inactivate microorganisms.

Findings were as follows:

On the average a 22 ug/ml sanguinarine chloride solution will inactivate cultures of the bacteria *Bacillus subtilis*, a 270 ug/ml solution cultures of *Escherichia coli*, a 540 ug/ml solution cultures of *Klebsiella pneumoniae*, a 590 ug/ml solution cultures of *Proteus vulgaria*, a 70 ug/ml solution cultures of Staphylococcus aureus, a 393 ug/ml solution cultures of *Streptococcus faecalis*, and a 161 ug/ml solution cultures of *Streptococcus mutans* (see Table I).

Further on the average a 150 ug/ml and a 20 ug/ml solution also inactivates the cultures of yeasts *Candida albicans* and *Saccharomyces cerevisiae*. A considerably lower concentration than the inactivation concentration of the drug preparation is useful as a growth inhibitor of the same organisms.

In addition, on the average a concentration of sanquinarine chloride presented in Table III was sufficient per cubic centimeter of media, to inhibit growth of some fungi known to belong to the group of ringworm producing organisms.

TABLE III

| Microorganisms | Mean Inhibiting Dose of Sanguinarine Chloride in μg/ml of Media |
|---|---|
| *Microsporum canis* | 867 |
| *Microsporum nanum* | 650 |
| *Trichophyton metagrophytes* | 900 |
| *Trichophyton schoenleini* | 467 |
| *Trichophyton terrestre* | 467 |
| *Trichophyton vanbreuseghemi* | 750 |

The basic preparations were, on numerous occasions, also tested on a variety of animals and also humans infected with ringworm and athletes foot fungus. It was found that preparations containing snguinarine chloride will considerably hasten recovery from ringworm infection and facilitate rapid healing of lesions. Results of clinical tests run by numerous dentists and dental institutions confirm that regular application of the composition of the instant invention to teeth surfaces will reduce the incidence of dental caries and the use on gums either by packing of irrigations will prevent or rapidly cure periodontal disease or microbial infections of the gums and surrounding tissues.

Application of the compositions of the present invention to cold sores immensely hastens the healing process. Cold sores dry up and heal in a few days.

When animals suffering from scours are treated internally with preparations containing sanguinarine chloride the recovery rate exceeds that of the antibiotics commonly used for the purposes of treating scours.

What is claimed is:

1. A method for treating dental carries in mammals comprising topically applying to the affected area an effective amount of the following composition:
  a. from about 0.1 to about 10% by weight of a hydrochloric acid salt of sanguinarine;
  b. from about 2% to about 60% by weight of zinc chloride;
  c. the remainder being a solvent selected from the group consisting of water, glycerine, propylene glycol, petrolatum, and $C_1$-$C_6$ alcohols.

2. The method of claim 1 wherein the sanguinarine salt present in the amount of 0.1% and the zinc chloride is present in the amount of 2.7%.

3. The method of claim 2 wherein the solvent is glycerine.

4. A method for treating periodontal disease in mammals comprising topically applying to the affected area an effective amount of the following composition:
   a. from about 0.1 to about 10% by weight of a hydrochloric acid salt of sanguinarine;
   b. from about 2% to about 60% by weight of zinc chloride;
   c. the remainder being a solvent selected from the group consisting of water, glycerine, propylene glycol, petrolatum, and $C_1$–$C_6$ alcohols.

5. The method of claim 4 wherein the sanguinarine salt is present in the amount of 0.1% and the zinc chloride is present in the amount of 2.7%.

6. The method of claim 5 wherein the solvent is glycerine.

7. A method for treating gingivitis and periodontitis in mammals comprising topically applying to the affected area an effective amount of the following composition:
   a. from about 0.1 to about 10% by weight of a hydrochloric acid salt of sanguinarine;
   b. from about 2% to about 60% by weight of zinc chloride;
   c. the remainder being a solvent selected from the group consisting of water, glycerine, propylene glycol, petrolatum, and $C_1$–$C_6$ alcohols.

8. The method of claim 7 wherein the sanguinarine salt is present in the amount of 0.1% and the zinc chloride is present in the amount of 2.7%.

9. The method of claim 8 wherein the solvent is glycerine.

10. A method for treating gingivitis in mammals comprising topically applying to the affected area an effective amount of the following composition:
    a. from about 0.1 to about 10% by weight of a hydrochloric acid salt of sanguinarine;
    b. from about 2% to about 60% by weight of zinc chloride;
    c. the remainder being a solvent selected from the group consisting of water, glycerine, propylene glycol, petrolatum, and $C_1$–$C_6$ alcohols.

11. The method of claim 10 wherein the sanguinarine salt is present in the amount of 0.1%, and the zinc chloride is present in the amount of 2.7%.

12. The method of claim 11 wherein the solvent is glycerine.

* * * * *